United States Patent [19]
Eldegheidy

[11] Patent Number: 4,639,316
[45] Date of Patent: Jan. 27, 1987

[54] AUTOMATIC LIQUID COMPONENT SEPARATOR

[75] Inventor: Mourad M. Eldegheidy, Raleigh, N.C.

[73] Assignee: Becton, Dickinson and Company, Franklin Lakes, N.J.

[21] Appl. No.: 681,771

[22] Filed: Dec. 14, 1984

[51] Int. Cl.⁴ ............................................. B01D 13/00
[52] U.S. Cl. .............................. 210/416.1; 210/433.2; 210/927
[58] Field of Search ............... 210/321.1, 416.1, 433.2, 210/927

[56] References Cited

U.S. PATENT DOCUMENTS

| | | | |
|---|---|---|---|
| 3,211,645 | 10/1965 | Ferrari . | |
| 3,485,751 | 12/1969 | Herrmann et al. | 210/321 X |
| 3,489,145 | 1/1970 | Judson et al. . | |
| 3,512,940 | 5/1970 | Shapiro | 210/359 X |
| 3,556,302 | 1/1971 | Agranot | 210/321 |
| 3,567,028 | 3/1971 | Nose | 210/232 |
| 3,567,031 | 3/1971 | Loeffler | 210/321 |
| 3,687,296 | 8/1972 | Spinosa et al. | 210/406 |
| 3,705,100 | 12/1972 | Blatt et al. | 210/321 |
| 4,001,117 | 1/1977 | Trechsel | 210/180 |
| 4,131,549 | 12/1978 | Ferrara | 210/359 |
| 4,191,182 | 3/1980 | Popovich et al. | 210/90 X |
| 4,212,742 | 7/1980 | Solomon et al. | 210/247 |
| 4,343,705 | 8/1982 | Legg | 210/637 |
| 4,490,256 | 12/1984 | Nussbaumer et al. | 210/927 X |
| 4,492,634 | 1/1985 | Villa-Real | 210/927 X |

OTHER PUBLICATIONS

Porter, M. C. et al, "Membrane Ultrafiltration", Chem. Tech., Jan. 1971, pp. 56-63.

Primary Examiner—David Sadowski
Attorney, Agent, or Firm—Robert P. Grindle

[57] ABSTRACT

A device in the form of a sealed transparent tube comprised of glass, for example, is provided for separating the fraction containing cells and cell free fraction of a liquid, such as blood, automatically upon introduction into the device, and without the need for any separate driving force. The device separates whole non-anticoagulated blood, for example, very rapidly upon introduction into the device. The device utilizes a cross-flow filtration area together with a vacuum force applied to the device during manufacture to cause immediate and rapid separation.

9 Claims, 7 Drawing Figures

AUTOMATIC LIQUID COMPONENT SEPARATOR

BACKGROUND AND STATEMENT OF THE INVENTION

This invention relates generally to devices for separating the heavy and light fractions of liquids and particularly for separating the particulate and non particulate fractions of blood. More particularly, this invention relates to self-contained devices for the automatic rapid separation of the cellular components of a blood sample from the plasma thereof in a rapid fashion prior to the introduction of any anticoagulants to a blood sample so collected. The device is arranged to provide the automatic rapid separation in little more than 30 seconds as the sample is introduced into the container.

The device is, preferably, comprised of a glass tube similar to a conventional evacuated blood collection tube ordinarily utilized for the collection of blood samples for subsequent investigation in a clinical lab. The device incorporates a membrane filter to provide a cross-flow filtration of the blood sample over the area in rapid fashion. Moreover, the device has imparted thereto during the manufacture thereof a vacuum to the internal chamber of the tube. When the sample of interest is taken and introduced into the device of the invention, the blood sample flows through a channel and over the membrane filter, creating a pressure differential high wall shear rate which in turn causes a rapid separation of the cell free fraction from the cell containing fraction of the blood sample. Thus, in substantially less than one minute after taking the sample from a patient, the components of the blood sample are properly separated without the need for any outside instrument for providing a separate driving force, such as a separate positive pressure drive for creating the pressure differential necessary to cause the separation.

U.S. Pat. Nos. 3,705,100; 4,212,742; 3,556,302; 3,211,645; 4,191,182 and 4,343,705 are representative of patents teaching conventional cross-flow filtration methodology. However, in each of these patents, the devices utilized require an applied pressure driving force from a separate source across the membrane filter in order to bring about the proper separation.

By contrast, with the invention here, a built-in vacuum is applied to a simple tubular device during the manufacture thereof, which vacuum serves to provide the proper separation of the components of the liquid sample in question, automatically, and in a very rapid automatic manner. Thus, a very simple throw-away device is provided for making such a separation rapidly by the physician himself or a medical technologist without the need for expensive equipment. The invention is a device in the form of a simple evacuated tube, closed with a stopper, containing an arrangement in accordance with this invention for providing a surface area for cross-flow filtration. The open end of the tube is closed by the stopper which is arranged to be penetrated by the needle of a syringe for the introduction therethrough of a sample to be separated.

The stopper is configured somewhat differently from the usual stopper in that it provides an indentation in the lower surface thereof which faces the inside of the evacuated container when in place. Inserted into this indentation in the lower surface of the penetrable stopper is an arrangement, in accordance herewith, including a membrane filter for providing the rapid separation of the cell containing fraction and cell free fraction of the sample in question. The membrane filter incorporated into this arrangement has the porosity required for the specific application and/or separation desired.

Once this arrangement has been constructed and the device is evacuated, when a sample is introduced by a needle cannula through the penetrable stopper of the evacuated tube, the sample spreads across the membrane, causing a pressure differential. The pressure differential created on opposite sides of the membrane has the effect of causing an automatic rapid separation of the cell containing and cell free fractions.

As purely illustrative of membranes which may be used for carrying out the separation in accordance with the device of the invention, one may note that dialyzing membranes and ultrafiltration membranes may be used. The pore diameter of the individual pores making up the membranes may be within the range of between about 0.1 micron and 1.2 microns, and preferably about 0.45 microns. Preferably, the pore diameter will be the maximum allowable diameter for achieving the desired separation for the materials under consideration.

Representative such membranes as discussed above, including a dialyzing membrane, type C, part number 105-1058, a product of Technicon Instruments Corporation, Tarrytown, N.Y. 10591. Ultrafiltration membranes may be of the U.F. Type C, Stock Number 1C9956 of Nuclepore Corporation, Pleasanton, Calif. 44566, or Ultrafiltration Membranes manufactured by Amicon Corporation, Lexington, Mass. 02173 such as Amicon Ultrafiltration Membrane types UM05, UM10, UM20, PM10, PM30, DM5, YM5, YM10 and YM30. As will be appreciated by practitioners-in-the-art of membrane technology, this technology has been well developed for fractionating biological fluids. Thus, this new device may be fully utilized for this membrane technology and provides a simple approach for achieving the desired results in an inexpensive and rapid manner.

One of the significant achievements with the device of the invention here is that the applied developed pressure over the membrane surface is within the range of between about 100–760 mm Hg, and preferably 500 mm Hg. As such, this reduced pressure reduces the possibility of hemolysis of blood cells during the separation procedure, while at the same time achieving the rapid separation of the cell containing and cell free fractions of the blood sample within a little more than 30 seconds.

With the foregoing objects in view, this invention will now be described in more detail and other objects and advantages thereof will become apparent from the following description, the accompanying drawings and the appended claims.

DETAILED DESCRIPTION OF THE INVENTION

Figure 1:
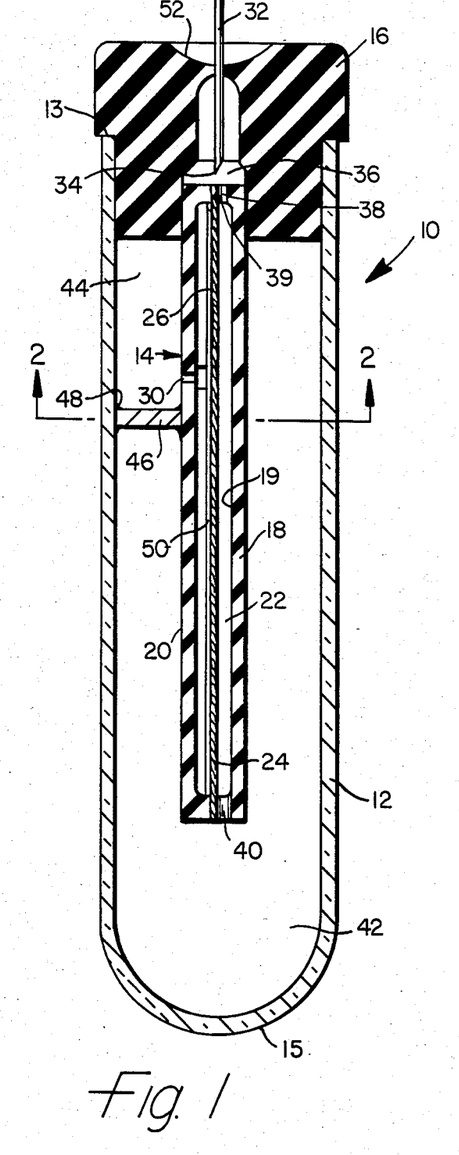
FIG. 1 is an enlarged longtudinal sectional view of a device incorporating the separation arrangement of the invention.

Referring to the drawings in which like reference characters refer to like parts throughout the several views thereof, FIG. 1 shows a representative evacuated tube assembly generally generally designated 10 embodying the invention herein. Assembly 10 includes a transparent tube 12, which may be comprised of a thermoplastic resin material such as polypropylene or polyethylene, for exmple. However, preferably, the tube will be comprised of glass since a glass tube will maintain the applied vacuum, in accordance herewith, for a longer storage life.

Tube 12 has suspended therein the separation assembly 14, in accordance with the invention. Tube 12 has an open end 13 and a closed end 15. As is shown in FIG. 1, the open end 13 is sealed with an elastomeric stopper 16. Generally, such stoppers are comprised of a natural or synthetic rubber material. Separation assembly 14 includes opposed walls 18, 20. Suspended between opposed walls 18 and 20 is a separation membrane 24 which is supported in assembly 14 against a grid 26. Grid 26, as will be described in more detail below, collects the blood passing through membrane 24 for distribution and subsequent passage through port 30 into the cell free fraction or filtrate collection chamber 44. The elongated surface of membrane 24 and the surface 19 of wall 18 define an initial blood sample collection passage 22, which is in the form of a rectangular channel, through which the sample flows along the surface of the membrane 24.

Thus, initially, a liquid sample such as blood is introduced through a cannula 32 which has been forced through stopper 16 to the extent where the forward point 34 of cannula 32 is in communication with area 36 defined by stopper 16. Thus, the sample passes through cannula 32 into area 36, wherein the blood is caused to flow through passage 38 under the vacuum imparted to the entire internal chamber of tube 12. Thus, the blood flows downwardly through chamber 22 along membrane filter 24. As this happens, a pressure differential is built up on each side of the membrane 24/grid 26 assembly, so that the cell free fraction of a blood sample is caused to flow through the membrane, and into the channels 50 of the grid 26 for passage through orifice 30 into cell free collection area 44. The cell containing fraction passes through port 40 into chamber 42.

Figure 2:
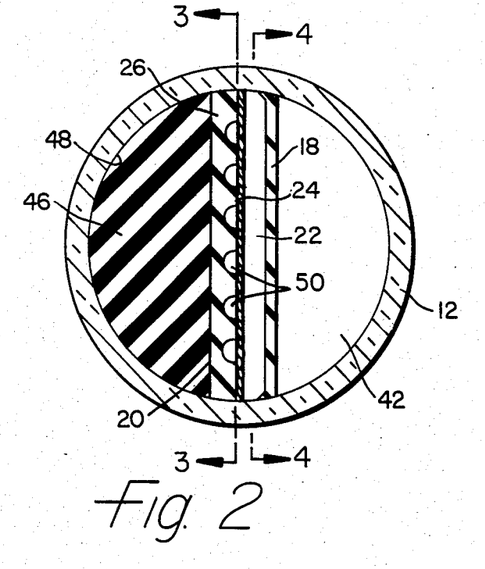
FIG. 2 is a cross-sectional view taken along lines 2—2 of FIG. 1.

As can be seen in FIG. 1, the separation assembly 14 is press fit into the lower portion of area 36 of stopper 16 for support in tube 12. Extending from one surface of wall 20 of assembly 14 is a semi-circular divider panel 46 defining and separating cell containing fraction chamber 42 from the cell free fraction chamber 44. As can best be seen in FIG. 2, divider panel 46 is semi-circular and extends from wall 20 to the internal surface of tube 12. It is within the purview of the invention that the outer semi-circular edge of the divider panel 46 has a continuous elastomer bead 48 for engaging in sealing engagement the internal surface of the tube 12, for providing a sealing separation between chambers 42 and 44. Alternatively, an adhesive may be utilized to join the outer edges of divider panel 46 with the internal surface or wall of tube 12.

As will be understood by practitioners-in-the-art, the assembly of the separator device of the invention will take place in a different manner, depending upon whether an elastomer bead 48 is utilized for sealing the two chambers 42, 44 from each other or an adhesive is utilized. That is, the assembly may be assembled with the separation portion thereof inserted initially for providing a joining of the outer surface of separation panel 46 with the internal wall of tube 12, if an adhesive is to be used. Subsequently, insertion of stopper 16 takes place partially during the evacuation of the tube in a conventional manner, as is well known by practitioners-in-the-art for creating evacuated blood collection tubes, followed by final seating of the stopper 16. Alternatively, separated assembly 14 may be press fit into stopper 16, and inserted simultaneously with the insertion of stopper 16 and the application of a vacuum to the assembly, if a sealing elastomer bead 48 is utilized for providing a sealing separation at the outer edge of the divider panel 46, for engaging the internal surface of tube 12.

Figure 3:
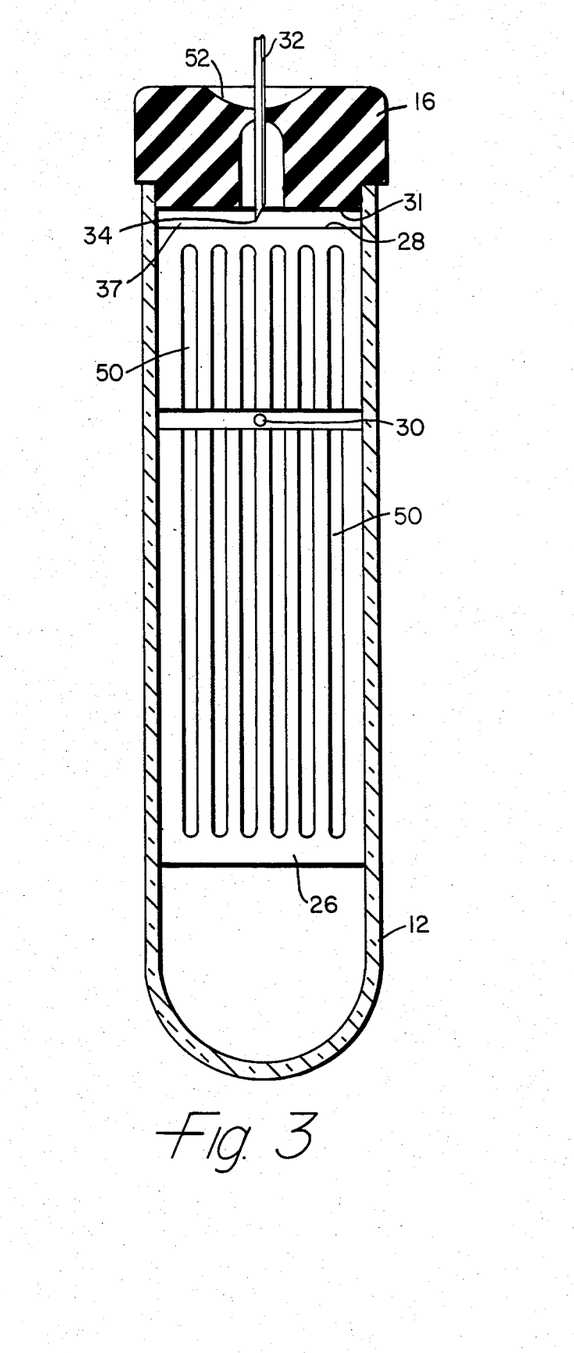
FIG. 3 is a sectional view taken along lines 3—3 of FIG. 2.

Referring to FIG. 3, the grid panel 26 surface configuration is shown. That is, a plurality of channels 50 are spaced evenly across panel 26 for receiving the cell free component of the liquid being separated by the device. The channels 50 are arranged to collect and distribute the cell free fraction to the orifice 30 under the action of the vacuum applied to the device, wherein the cell free fraction passes through orifice 30 into chamber 44, as shown in FIG. 1. As can be seen further in FIG. 3, stopper 16 includes an upper well 52, as well known in the art, for providing a thinner diaphragm area centrally in stopper 16 for inserting and passing a cannula point 34 therethrough. The top edge 28 of panel 26 stops short of the bottom edge 31 of area 36 in stopper 16 to define a rectangular void space 37.

Figure 4:
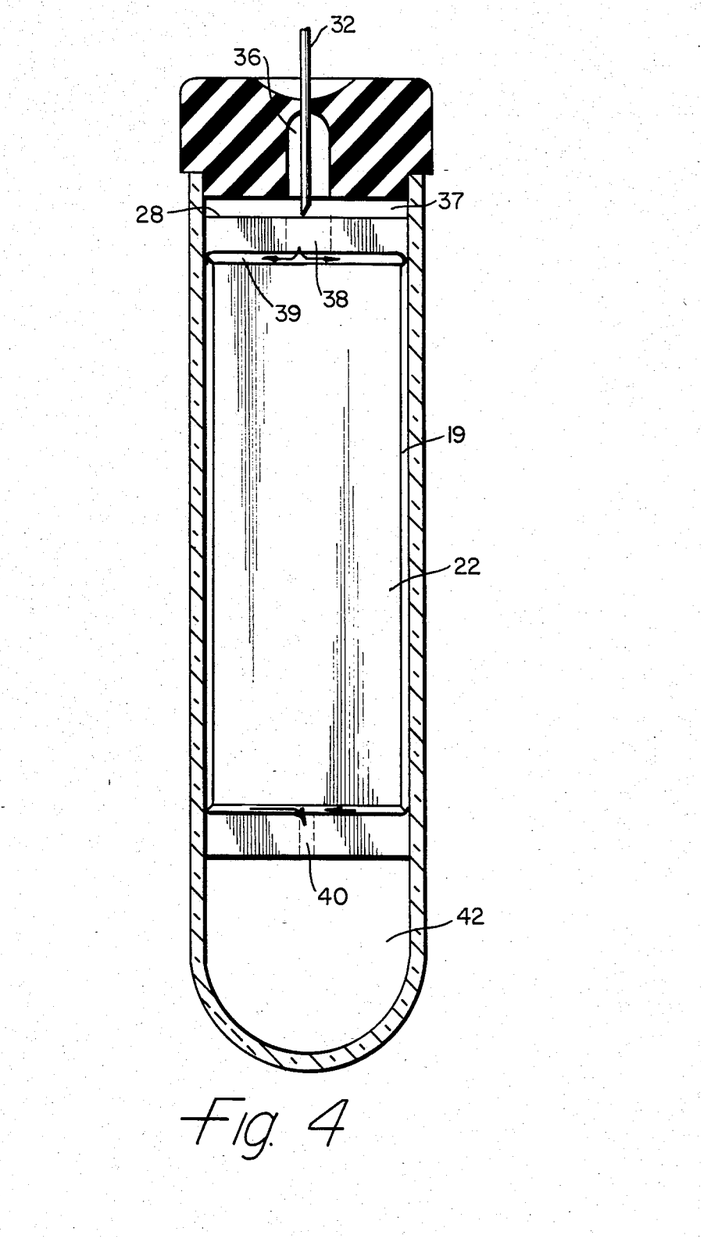
FIG. 4 is a sectional view taken along lines 4—4 of FIG. 2.

Referring now to FIG. 4, blood introduced by cannula 32, as shown in FIG. 4, passes into the area 36 defined in the bottom surface of stopper 16. Subsequently, from the area or chamber 36 in stopper 16, the blood passes to the inlet port 38, which may be eliptical where it is guided onto the plate surface 19 forming the internal surface of wall 18 by an elliptical slot 39. Surface 19 is a liquid distribution surface for guiding sample flow over the entire surface of membrane 24. It is recessed to form channel 22, and receives the sample distribution from elliptical slot 39. As purely illustrative of dimensions for channel 22, it may be rectangular and 1.5 centimeters wide by 10 centimeters long. It is recessed to a depth within the range of between about 0.01 and 0.03 centimeters. This channel serves to help create the desired high wall shear rate in the sample which results in the separation of the cell containing fraction from the cell free fraction. Flow at the bottom of channel 22 passes through port 40, into chamber 42. Alternatively, channel 22 may have a tapered recess depth.

Figure 4A:
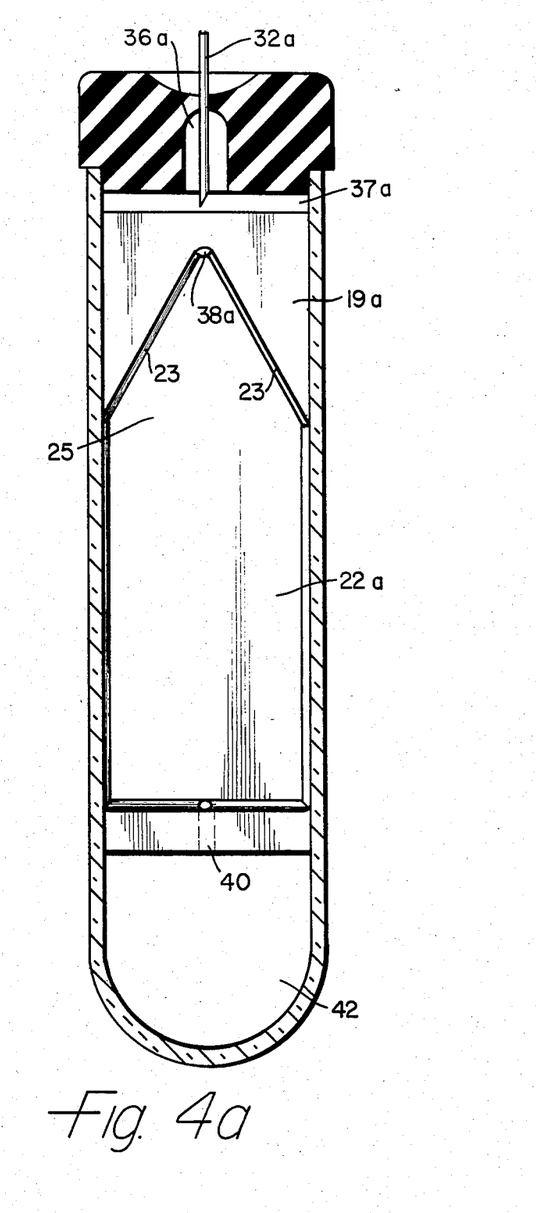
FIG. 4a is a view of the device similar to FIG. 4, but showing an alternative embodiment of sample distribution chamber.

FIG. 4a is an alternative embodiment of wall 19 designated 19a having a recessed distribution channel 22a. In this embodiment a round orifice 38a distributes the sample to be separated from area 37a to a recessed portion 25 in wall 19a of gradually increasing cross section defined by diverging walls 23. This configuration helps decrease initially transmembrane pressure across membrane 25 at the outset of separation. The angle of divergence is 20° from the axis of orifice 38a.

Figure 5:
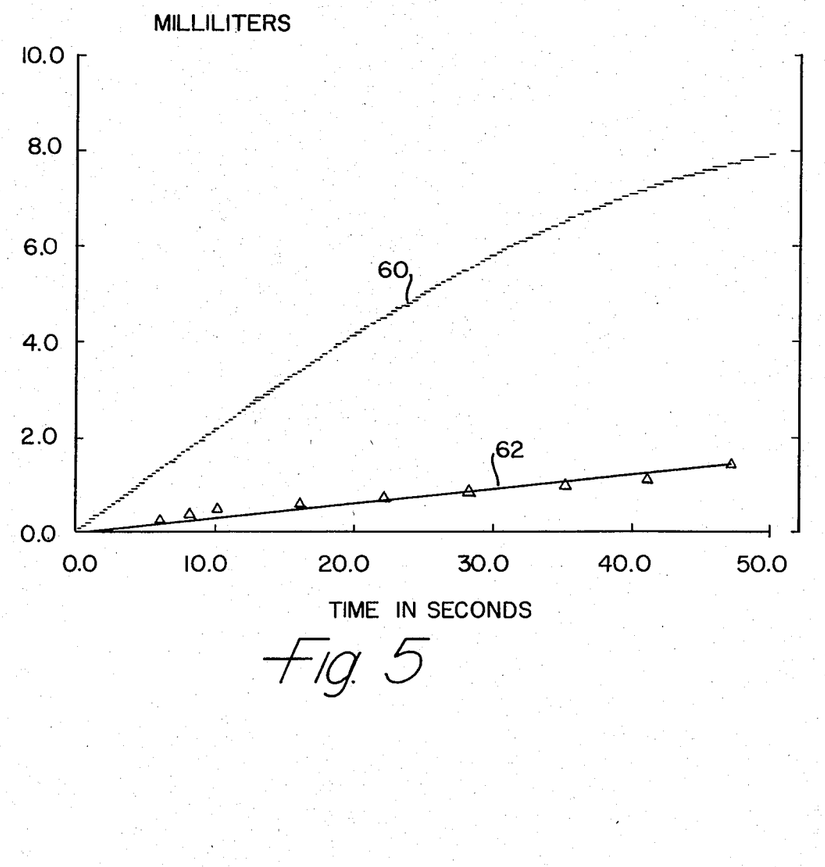
FIG. 5 is a graph illustrating the heavier/lighter fraction flow pattern separation of a representative sample in the device of the invention.

Referring now to FIG. 5, a graph is shown of an actual sample of blood inserted into the device of the invention. The ordinate is in milliliters, while the abscissa is in time, in seconds. The needle inserted through stopper 16 was a 22 gauge needle, and the blood sample was approximately 10 milliliters. The tube capacity was 12 milliliters which is similar in size to a conventional evacuated blood collection tube. As can be seen in FIG. 5, the line 60 is the heavy blood cell fraction of the sample introduced, while the line 62 is the lighter plasma fraction. As can be seen in FIG. 5, separation takes place immediately and is completed in less than 50 seconds. More importantly, most quantity of the sample is separated within 30 seconds. It should be noted, that during the taking and observation of the sample, that there was no discoloration or other indication of hemolysis in the cell free plasma fraction.

Figure 6:
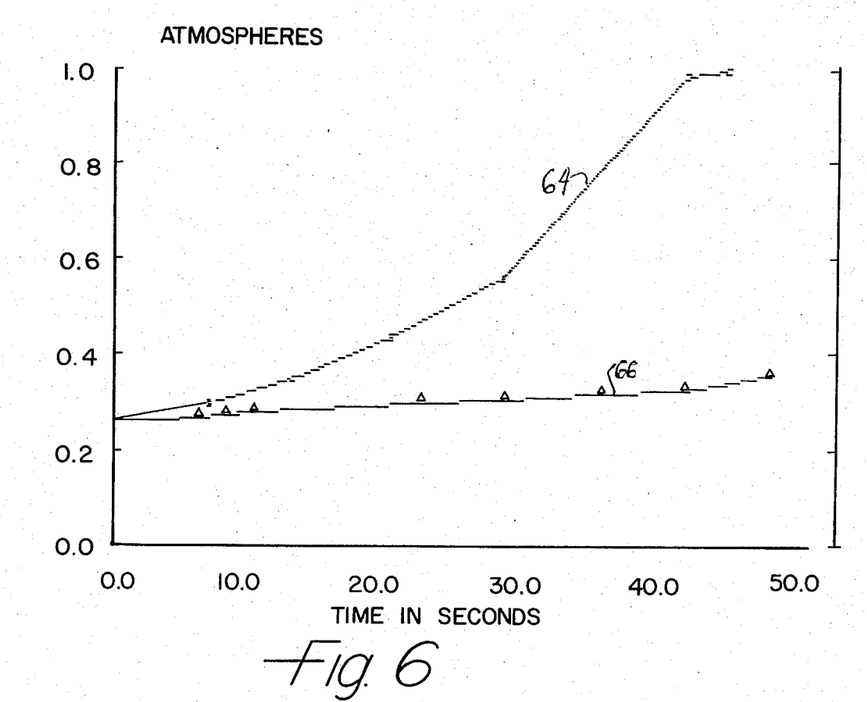
FIG. 6 is a graph showing the cell containing/cell free fraction profile of the same sample as FIG. 5.

Referring now to FIG. 6, a second graph is shown, showing the cell containing/cell free fraction blood reserve pressure profile, as an indication of the developed pressure differential between the separated common chambers of the device, even though the same vacuum is applied on both sides of the separation assembly during the assembly and manufacture thereof. As can be seen in FIG. 6, the cell containing fraction 64 pressure builds up rapidly to one atmosphere of mercury, from approximately a little less than three-tenths atmospheres, while the cell free fraction pressure 66 builds up only to about 0.4 atmospheres.

Thus, as will be appreciated from the above, there is provided in accordance with this invention, a simple uncomplicated throw-away device which is easily and inexpensively manufactured, for accomplishing a rapid separation of the cell containing and cell free fractions of a liquid and particularly, for example, the cell containing and cell free fractions of a blood sample. It will be appreciated that this device is particularly useful for a doctor and/or clinical laboratory where it is necessary to take a blood sample and obtain a rapid separation of the cell containing and cell free fractions of the blood sample taken. Moreover, it will be appreciated that this device is particularly appropriate for such purposes, since an anticoagulant is not required prior to separation. The device requires no separate applied force such as an instrument for applying pressure to a container for causing separation.

More importantly, no separate expensive arrangements or instrumentation is required in order to bring about this rapid and complete separation of the cell containing and cell free fractions of a blood sample immediately after the taking of the sample from a patient. The device achieves the simple separation procedure automatically, once the sample is introduced therein.

While the methods and apparatus herein disclosed form preferred embodiments of this invention, this invention is not limited to those specific methods and apparatus, and changes can be made therein without departing from the scope of the invention which is defined in the appended claims. That is, as discussed above, while the device was developed specifically for separating heavy and lighter components of a blood sample, the device is useful and appropriate for a simple fractionating separation of other biological fluids as well.

What is claimed is:

1. A device for the immediate separation of a blood sample into a cell containing and a cell free fraction of said blood sample characterized by (a) an elongated cylindrical tube having a closed end and an open end;
   (b) said tube defining an evacuated chamber;
   (c) an elastomeric stopper sealingly closing said open end, said stopper having a bottom surface;
   (d) a recess in the bottom surface of said stopper facing said evacuated chamber, said recess defining a sample receiving area;
   (e) a flat elongated separation assembly in said evacuated chamber;
   (f) said separation assembly positioned in said evacuated chamber to extend from said closed end of said tube to a point spaced from the open end thereof and having a length extending along the central axis of said tube;
   (g) said separation assembly separating said evacuated chamber into a cell free fraction receiving chamber and a cell containing fraction receiving chamber;
   (h) said elongated separation assembly comprising
      (1) a pair of spaced apart elongated walls;
      (2) said spaced apart walls defining a blood sample collection passage therebetween;
      (3) the first of said spaced walls containing a cell free fraction receiving distributor panel;
      (4) the second of said spaced walls containing a sample distribution chamber having first and second ends;
      (5) said sample distribution chamber connected to said sample receiving area at said first end and to said cell containing fraction receiving chamber at said second end;
      (6) a membrane separator positioned in said blood sample collection passage and extending along the length thereof;
      (7) said membrane separator having one side adjacent said cell free fraction receiving distributor panel and one side adjacent said sample distribution chamber;
      (8) said cell free fraction distributor panel having a plurality of spaced apart channels therein for receiving a cell free fraction passing through said membrane separator; and
      (9) means providing flow communication between said channels and said cell free fraction receiving chamber.

2. The device of claim 1, further characterized by
   (a) said membrane separator defining individual pores, wherein the diameter of the individual pores of said membrane separator is within the range of between about 0.1 and 2.2 microns.

3. The device of claim 2, further characterized by
   (a) said diameter is 0.45 microns.

4. The device of claim 1, further characterized by
   (a) a cannula receiving upper well in said stopper.

5. The device of claim 1, further characterized by
   (a) said tube is comprised of a member selected from the group consisting of glass, polyethyelene and polypropylene.

6. The device of claim 1, further characterized by
   (a) said sample distribution chamber is a recessed distribution channel recessed within the range of 0.01 and 0.03 centimeters.

7. The device of claim 6, further characterized by
   (a) said distribution channel is rectangular.

8. The device of claim 7, further characterized by
   (a) said distribution channel is 1.5 centimeters wide and 10 centimeters long.

9. The device of claim 6, further characterized by
   (a) said distribution channel includes an inlet area with gradually diverging walls.

* * * * *